United States Patent [19]

Gunther

[11] 4,162,942

[45] Jul. 31, 1979

[54] MONITORING ETHYLENE OXIDE STERILIZATION RESIDUAL WITH ENZYMES

[75] Inventor: Donald A. Gunther, Erie, Pa.

[73] Assignee: American Sterilizer Company, Erie, Pa.

[21] Appl. No.: 797,736

[22] Filed: May 17, 1977

[51] Int. Cl.$^2$ .................... C12K 1/00; G01N 31/14
[52] U.S. Cl. .................... 435/17; 23/232 R; 435/21; 435/28; 435/31
[58] Field of Search .............. 195/103.5 R, 103.5 M, 195/101; 23/232 R; 21/2

[56] References Cited

U.S. PATENT DOCUMENTS

| | | | |
|---|---|---|---|
| 3,597,235 | 8/1971 | Kramer | 426/324 |
| 3,738,811 | 6/1973 | Cheng | 23/232 R |
| 3,852,034 | 12/1974 | Gunther | 23/232 R |

OTHER PUBLICATIONS

Gunther, "Safety of Ethylene Oxide Gas Residuals part i", *American Journal of Hospital Pharmacy*, vol. 31, pp. 558-561 (1974).

Gunther, "Safety of Ethylene Oxide Gas Residuals Part ii", *American Journal of Hospital Pharmacy*, vol. 31, pp. 684-686 (1974).

Libicky, "Effect of Ethylene Oxide Sterilization on the Activity of some Organ Preparations. II Effect of Ethylene Oxide on Crystalline Pancreatic Enzymes High Pressure Sterilization", *Chem. Abstracts*, vol. 67, No. 25, pp. 10739-10740 (1967), Abs. #114012u.

*Primary Examiner*—Thomas G. Wiseman
*Attorney, Agent, or Firm*—Shanley, O'Neil and Baker

[57] ABSTRACT

A method for indicating possible biological hazard due to sterilization residual, e.g. ethylene oxide sterilization residual, involves extracting residual, contacting extracted residual with enzyme, and providing an indication of enzyme deactivation.

13 Claims, No Drawings

MONITORING ETHYLENE OXIDE STERILIZATION RESIDUAL WITH ENZYMES

BACKGROUND OF THE INVENTION

This invention relates to a method of monitoring sterilization residual, such as ethylene oxide sterilization residual, in articles which have been sterilized.

Ethylene oxide sterilization is commonly used in hospitals and the like for treating articles of plastic, paper, rubber or the like which cannot withstand steam sterilization. Typically, it involves humidifying the articles to be sterilized and then contacting them with ethylene oxide usually in admixture with an inert diluent such as dichlorodifluoromethane. Articles subjected to such sterilizing treatment have been found to contain ethylene oxide, ethylene chlorohydrin and ethylene glycol. These residual contaminants are referred to as ethylene oxide sterilization residual.

Ethylene oxide sterilization residual has been recognized as a problem. Articles used upon completion of ethylene oxide sterilization are considered unsafe because of such residual; (see, for example, "Evaluation of Sterilization By Gaseous Ethylene Oxide" by H. Stierli, M.S., et al, Public Health Monograph #68, p. 13, which refers to the severe chemical burns which can result from use of ethylene oxide sterilized rubber gloves which have not been aerated properly). Procedures were developed wherein such articles are quarantined on the shelf until the residual has been sufficiently desorbed, for example, for up to 168 hours. More recently, gas sterilizers have been used with aeration chambers having aeration cycles of, for example, 8-12 hours, to remove residual contaminants. The basic question presented is whether the possibility of biological hazard exists if the articles are put to use within what would be practical times considering hospital inventories.

Chemical analytical techniques can be used to quantitatively measure the various components which sterilization residual comprises and can be of benefit if properly relatable to other biological data. Such analysis has the disadvantage of requiring separate analyses for a number of components.

Also, various methods of toxicity testing for sterilant residues are known: for example, subcutaneous injection, implantation, topical tissue (including ocular) application. oral toxicity and intravenous injection. Such methods are referred to, for example, in the following: Wilson, John E., "Ethylene Oxide Sterilant Residues", *Bulletin of the Parenteral Drug Association,* 24, 226–234 (1970); Anderson, Shirley R., "Ethylene Oxide Residues in Medical Materials", *Bulletin of the Parenteral Drug Association,* 27, 49–57 (1973), McDonald, T. O. et al, "Acute Ocular Toxicity of Ethylene Oxide Ethylene Glycol, and Ethylene Chlorohydrin", *Bulletin of the Parenteral Drug Association,* 27, 153–164 (1973). These test methods are relatively cumbersome; time consuming, costly, and frequently not within the capability of certain laboratories especially hospital laboratories.

It is a primary objective of the present invention to provide a biological method for indicating possible biological hazard due to sterilization residual in an article, which method is practical in application and directly relatable to the end answer sought by such testing, i.e., safety for use.

BRIEF DESCRIPTION OF THE INVENTION

A basic contribution of the invention involves enzyme deactivation as an indicator of possible biological hazard. Enzymes are selected which are responsive, preferably in a gradable manner, to biologically harmful sterilization residual. Contact between such residuals and selected enzyme and reaction therebetween to deactivate enzyme, provides a practical indication of possible toxicity in sterilized articles which can be determinative of non-suitability for use, at that time.

A specific method for indicating possible biological hazard due to sterilization residual, comprises the steps of (a) selecting sterilized material for evaluation;

(b) contacting such material with extracting agent capable of extracting sterilization residual and capable of acting as a reaction vehicle for step (c), under conditions selected so as to extract a representative percentage of such residual;

(c) concurrently with or subsequent to step (b), contacting any extracted residual with enzyme capable of being deactivated by residual under conditions which permit residual to deactivate enzyme;

(d) providing an indication of resultant enzyme deactivation.

Enzyme deactivation can be utilized directly as a qualitative indication of possible hazard. Or, quantitative data can be elicited based on empirical standards.

In describing a specific embodiment of the invention, these methods are readily applied to evaluating the safety of articles sterilized with ethylene oxide.

DETAILED DESCRIPTION OF THE INVENTION

The step of selecting sterilized material to be evaluated (step (a) set forth above) is practical so as to alleviate the need to test every article in a batch of articles which have been sterilized. In other words, the selection can be, for example, of a representative article or articles. Typically, the selection is of an article which is difficult to aerate such as an article in which the residual desorbs slowly, or in which reaction products such as ethylene chlorohydrin or ethylene glycol are likely to be formed (such as PVC). The selection can be of a portion of one such articles. The selection can also be of a product manufactured especially for placement in the sterilizer along with articles being sterilized such that evaluation of the product will be indicative of the safety of the entire sterilizer load.

The step of contacting the article being tested with extracting agent (step (b) set forth above) can involve contacting the selected sterilized material with extracting agent capable of extracting ethylene oxide sterilization residual and capable of acting as a reaction vehicle for the reaction (enzyme deactivation) described below. Suitable extracting agents include, for example, distilled water, isotonic saline and substrate solution. This step is preferably carried out to extract one hundred percent of the ethylene oxide sterilization residual. This is carried out, for example, by use of a ratio of extracting agent to material being tested ranging from 10 milliliters per gram to 50 milliliters per gram, a temperature ranging from 5° C. (40° F.) to 65° C. (150° F.), a time period ranging from 1 hour to 24 hours, and stirring. Alternatively, conditions can be controlled to extract a lesser percentage of the ethylene oxide sterilization residual which is representative of the total. In other words, the percentage extracted is required to be a representative percentage whether one hundred percent or less.

The reaction step (step (c) set forth above) involves the use of enzyme capable of being deactivated by biologically hazardous residual. Such enzyme can be, for example, selected from the group consisting of oxidation enzymes, transferases, and hydrolases. Suitable oxidation enzymes include for example, peroxidase, alcohol dehydrogenase, lactate dehydrogenase, and glucose oxidase. Suitable transferases include for example, creatine phosphokinase, pyruvate kinase, glycerol kinase, and hexokinase. Suitable hydrolases include, for example, acid phosphatase, beta amylase, lipozyme, and urease. In a preferred reaction step, preselected conditions are utilized. These conditions are preselected so as to be the same conditions (e.g. amount of enzyme, reaction temperature and reaction time) as have been or are used to obtain information on known samples. Preferably, these conditions comprise an amount of enzyme ranging from 10 micrograms to 1000 micrograms (on the basis of reaction with contaminant from a 1 gram sample), a reaction time ranging from 1 hour to 24 hours and a reaction temperature ranging from 5° C. to 65° C. The extracting and reacting steps (steps (b) and (c) set forth above) can be carried out concurrently (that is, the reacting step can be carried out during at least a portion of the extracting step), for example, by admixing the enzyme with the extracting agent while such agent is still extracting residual. Preferably, the reacting step is carried out subsequent to the extracting step; this minimizes the possibility of the enzyme being deactivated by the material being tested.

The step of providing an indication of resultant enzyme deactivation (step (d) set forth above) can involve for example, determining loss of enzyme activity, for example, using an assay procedure to measure the percentage of enzyme deactivated. Worthington Enzyme Manual (1972), Worthington Biochemical Corporation, Freehold, New Jersey and EM Diagnostic Tests Operators Instructions, EM Laboratories, Inc., 500 Executive Boulevard, Elmsford, New York are comprehensive treatises disclosing assay procedures for measuring enzyme activity which are readily adapted for use herein. See, for example, page 43 of Worthington Enzyme Manual (1972) for an assay procedure for peroxidase found to be preferred herein which involves using the enzyme, if active, to decompose hydrogen peroxide thereby releasing oxygen which decolorizes the dye, 0-dianisidine.

The indication of resultant enzyme deactivation can be used qualitatively. In other words, if an amount of enzyme deactivation is determined which is relatively high, for example, greater than 5%, the sterilized articles can be assumed to be unsafe.

The indication of resultant enzyme deactivation can also be used in a more quantitative sense by comparison with information obtained on known samples relating loss of enzyme activity and presence of residual (contaminant) to indicate an absence of residual ethylene oxide or a small amount of residual ethylene oxide or an amount of residual ethylene oxide less than some preselected limit chosen as safe. Such comparison gives results, for example, in terms of the maximum level of residual ethylene oxide which can be present (that is, results based on the assumption that all the loss of enzyme activity is due to residual ethylene oxide) or in terms of whether such maximum level exceeds some preselected limit. In the case of determining the maximum level of residual ethylene oxide which is present, the information used for comparative purposes is preferably obtained by reaction of the enzyme being used under preselected conditions with solutions containing various amounts of contaminant (to establish enough data, for example, to plot a curve of percent deactivation vs. ppm contaminant, preferably on a one gram sample basis). In the case of determining if the maximum level of ethylene oxide which is present exceeds some preselected limit, the information used for comparative purposes is preferably obtained by reacting the enzyme for which data is being gathered under the preselected conditions with a solution containing an amount of contaminant corresponding to the preselected limit. The preselected conditions used to establish the information compared with are the same as those used in the reaction step (step (c) above). As indicated in the reaction step described above, these preferably comprise an amount of enzyme ranging from 10 micrograms to 1000 micrograms (on the basis of reaction with contaminant from a 1 gram sample), a reaction temperature ranging from 5° C. to 65° C. and a reaction time ranging from 1 hour to 24 hours.

The following examples are illustrative of the invention but are not to be construed as limiting applicability of the invention to particular sterilized articles or the particulars of steps enunciated.

EXAMPLE I

Ethylene oxide sterilization is carried out on a batch of articles. The sterilization cycle consists of adding water for 1 minute to obtain a 100% relative humidity, charging the sterilizer with ethylene oxide in admixture with dichlorodifluoromethane (12/88) over a 15 minute period to 15 psig, exposing the articles to ethylene oxide for 3 hours and then relieving the pressure to atmospheric. The average ethylene oxide concentration used in the sterilizer is 421 milligrams per liter.

Four identical pieces of PVC tubing (each weighing one gram) are selected from the batch of articles being sterilized as being representative of the articles sterilized.

Two of the tubing pieces are selected for immediate testing, one by the method of this invention and one by chemical analysis. The other two are subjected to an 8 hour aeration at 50° C. and then are tested, one by the method of this invention and one by chemical analysis.

The pieces of tubing treated in accordance with the method of this invention are each extracted using 10 ml of distilled water over a 16 hour period at 37° C. with stirring. In each case, the extract is then separated, peroxidase is admixed to provide 100 micrograms enzyme, and reaction is carried out for 1 hour at 25° C. In each case, the loss of enzyme activity is determined using the procedure briefly described above and set forth in more detail at page 43 of Worthington Enzyme Manual (1972). Such determinations indicate that the loss of enzyme activity for the piece of tubing not aerated is >15% and the loss of enzyme activity for the piece of tubing which is aerated is <5%. These figures are compared to a curve obtained by measuring the loss of peroxidase activity in solutions of distilled water containing 10 ppm, 100 ppm, 1000 ppm and 10,000 ppm ethylene oxide (data obtained using solutions containing 100 micrograms enzyme, a reaction time of 1 hour and a reaction temperature of 25° C. and adjusting so that the data is on a one gram sample basis). Such comparison indicates the non-aerated sample of tubing contains at least 1000 ppm ethylene oxide assuming that all deactivation is caused by ethylene oxide and that the sample of tubing tested after aeration contains a maximum of 10 ppm ethylene oxide indicating aeration for 8 hours at 50° C. satisfactory for the type of load. Chemical analysis indicates that the piece of tube selected before aeration contains 11,300 ppm residual ethylene oxide and that the piece of tube which is aerated contains no residual ethylene oxide thereby confirming the results obtained by the method of the invention.

When in the above example, reaction is carried out simultaneously with extraction, substantially equal results are obtained.

When, in the above example, isotonic saline or substrate solution is substituted for the distilled water extracting agent substantially equal results are obtained.

EXAMPLE II

Example I is duplicated except that creatine phosphokinase is substituted for peroxidase and the only data for comparison purposes is that 1000 ppm ethylene oxide (on a one gram sample basis) deactivates 8.2% of the enzyme. The testing indicates that in the sample subjected to the 8 hour aeration, the loss of activity of enzyme is <5% indicating the presence of substantially less than 1000 ppm residual ethylene oxide.

Carrying out of the test a number of times indicates creatine phosphokinase is very sensitive to detergent requiring it to be used on articles not cleaned with detergent or very thoroughly rinsed.

EXAMPLE III

Acid phosphatase reacts with a distilled water solution of ethylene oxide (10,000 ppm) over a 3 hour period at 25° C. whereby there is loss of enzyme activity (20% inactivation) indicating the usefulness of acid phosphatase in the method of the present invention.

The term "enzyme deactivation" is used herein to mean the loss of the ability of the enzyme to initiate a specific chemical reaction, for example, active peroxidase will cause hydrogen peroxide to decompose and oxidize the dye 0-dianisidine; deactivated peroxidase will not.

While the invention has been described above in detail with respect to residual ethylene oxide, it is clear that it provides utility for monitoring other biologically-antagonistic residual contaminants, for example residual of other sterilants such as formaldehyde or propylene oxide. In view of the variations that are readily understood to come within the limits of the invention, such limits are determined by the scope of the claims.

What is claimed is:

1. A method for determining the presence of ethylene oxide residual in a material previously sterilized with ethylene oxide comprising
   (a) contacting said material with an extracting agent so as to remove at least a portion of any ethylene oxide sterilization residual present in the material,
   (b) reacting said extracted ethylene oxide sterilization residual with enzyme which becomes inactivated by ethylene oxide sterilization residual, and
   (c) determining the loss of enzyme activity.

2. Method as recited in claim 1, in which the sterilized material is a product manufactured for use in the test of this method to be placed in the sterilizer along with articles being sterilized.

3. Method as recited in claim 1, in which the sterilized material is a portion of an article which has been sterilized.

4. Method as recited in claim 1, in which step (a) is carried out utilizing a ratio of extracting agent to material ranging from 10 milliliters per gram to 50 milliliters per gram, a temperature ranging from 5° C. to 65° C., a time period ranging from 1 hour to 24 hours and stirring.

5. Method as recited in claim 4, in which, the extracting agent is selected from the group consisting of distilled water, isotonic saline and substrate solution.

6. Method as recited in claim 1, in which the enzyme is selected from the group consisting of oxidation enzymes, transferases and hydrolases.

7. Method as recited in claim 6, in which the enzyme is peroxidase.

8. Method as recited in claim 6, in which the enzyme is creatine phosphokinase.

9. Method as recited in claim 6, in which the enzyme is acid phosphatase.

10. Method as recited in claim 1, in which step (b) is carried out after step (a).

11. Method as recited in claim 10, in which step (b) is carried out under preselected conditions.

12. Method as recited in claim 11, in which the preselected conditions comprise a temperature ranging from about 5° C. to about 65° C. and a time period ranging from about 1 hour to about 24 hours.

13. Method as recited in claim 1 wherein steps (a) and (b) are carried out concurrently.

* * * * *